(12) United States Patent
Moran

(10) Patent No.: US 10,695,639 B2
(45) Date of Patent: Jun. 30, 2020

(54) SPEED TRACKER

(71) Applicant: Robert Moran, Belmont, MA (US)

(72) Inventor: Robert Moran, Belmont, MA (US)

( * ) Notice: Subject to any disclaimer, the term of this patent is extended or adjusted under 35 U.S.C. 154(b) by 34 days.

(21) Appl. No.: 15/706,276

(22) Filed: Sep. 15, 2017

(65) Prior Publication Data

US 2018/0078839 A1    Mar. 22, 2018

Related U.S. Application Data

(60) Provisional application No. 62/395,887, filed on Sep. 16, 2016.

(51) Int. Cl.
| | | |
|---|---|---|
| *A63B 24/00* | (2006.01) | |
| *A63B 69/00* | (2006.01) | |
| *A63B 69/32* | (2006.01) | |
| *A63B 71/06* | (2006.01) | |
| *G01P 3/66* | (2006.01) | |

(52) U.S. Cl.
CPC .......... *A63B 69/32* (2013.01); *A63B 24/0062* (2013.01); *A63B 69/004* (2013.01); *A63B 71/0622* (2013.01); *A63B 2220/30* (2013.01); *A63B 2220/53* (2013.01); *A63B 2220/64* (2013.01); *A63B 2225/50* (2013.01); *G01P 3/66* (2013.01)

(58) Field of Classification Search
CPC . A63B 69/32; A63B 71/0622; A63B 24/0062; A63B 69/004; A63B 2220/64; A63B 2220/30; A63B 2225/50; A63B 2220/53
See application file for complete search history.

(56) References Cited

U.S. PATENT DOCUMENTS

| | | | | |
|---|---|---|---|---|
| 4,824,107 A | * | 4/1989 | French | A63B 71/06 273/454 |
| 4,953,875 A | * | 9/1990 | Sudit | F41J 5/044 273/373 |
| 4,959,807 A | * | 9/1990 | Thomspon | G01P 3/66 324/178 |
| 5,741,970 A | | 4/1998 | Rubin | |
| 6,308,578 B1 | * | 10/2001 | DeRose | G01L 5/0052 73/780 |
| 6,554,284 B2 | * | 4/2003 | Chou | A63B 63/00 273/371 |

(Continued)

FOREIGN PATENT DOCUMENTS

WO    2015164382 A1    10/2015

OTHER PUBLICATIONS

International Search Report and Written Opinion dated Dec. 1, 2017, 8 pgs.

*Primary Examiner* — Sundhara M Ganesan
(74) *Attorney, Agent, or Firm* — Glen E. Shumann; Moss & Barnett

(57) ABSTRACT

The present invention is a device for measuring and displaying the speed, force, rate and/or frequency that an object or a body part strikes a target. The present invention includes an impact sensor, transmitter, computer and display. The sensor includes layers of alternating conductive and nonconductive material that are wrapped around the target. The conductive layers of fabric generate electrical impulses when struck and serve as data points that are interpreted by the computer to derive statistics about a strike against the target.

12 Claims, 10 Drawing Sheets

(56) References Cited

U.S. PATENT DOCUMENTS

| | | | |
|---|---|---|---|
| 9,027,415 B2* | 5/2015 | Tsai | G01L 5/0052 |
| | | | 73/862.041 |
| 9,074,925 B2 | 7/2015 | Koppel | |
| 9,289,177 B2 | 3/2016 | Kassim | |
| 9,310,264 B2 | 4/2016 | David | |
| 9,360,362 B2 | 6/2016 | Metzger | |
| 9,381,064 B2 | 7/2016 | Tsusaka | |
| 9,410,984 B2 | 8/2016 | Amemiya | |
| 9,775,396 B1* | 10/2017 | Olivares Velasco | A42B 3/046 |
| 2008/0215285 A1* | 9/2008 | Bucar | A63B 69/201 |
| | | | 702/139 |
| 2010/0144414 A1* | 6/2010 | Edis | A63B 24/0006 |
| | | | 463/8 |
| 2012/0053016 A1* | 3/2012 | Williamson | A63B 24/0062 |
| | | | 482/8 |
| 2012/0144934 A1 | 6/2012 | Russell | |
| 2012/0198593 A1 | 8/2012 | Beck | |
| 2013/0307989 A1 | 11/2013 | Stone | |
| 2014/0190754 A1 | 7/2014 | Bucher | |
| 2015/0087925 A1 | 3/2015 | Pedley | |
| 2015/0177085 A1 | 6/2015 | Herhaus | |
| 2015/0211891 A1 | 7/2015 | Robert | |
| 2015/0316433 A1 | 11/2015 | Von Waitz | |
| 2016/0109306 A1 | 4/2016 | Janssen | |
| 2016/0199716 A1 | 7/2016 | Nergaard | |
| 2016/0202130 A1 | 7/2016 | Rowe | |
| 2016/0235387 A1 | 8/2016 | Murray | |
| 2016/0241699 A1 | 8/2016 | Milnark | |
| 2019/0388756 A1* | 12/2019 | Marciano | A63B 71/06 |

* cited by examiner

| Thickness (in*) | Low Density | High Density | Cross Linked |
|---|---|---|---|
| 1/4 | 12200 | 12250 | 12660 |
| 3/8 | | 12350 | |
| 1/2 | 12400 | 12450 | |
| 3/4 | | 12550 | |
| 1 | 12600 | 12650 | |

FIG. 7

| ID | Requirement | Verification Description |
|---|---|---|
| 1. | Technical | |
| 1.1 | The design of this system shall be "production ready". This design shall NOT be a prototype. | Inspection of Final Design ready for production documents, i.e. drawings, bill of materials that reference material and component supplier's quotations of Requirement 1.1, software code, etc. |
| 1.1 | The Technical Performance Measure (TPM) of the display in miles per hour (mph) shall be rounded to the one miles per hour, i.e. 50.50 miles per hour shall be rounded to display 51 miles per hour. Likewise, 50.49 miles per hour shall be rounded to display 50 mph. | (1) Observation of display.<br>(2) Display shows miles per hour value to the nearest one mile per hour. |
| 1.2 | The system shall measure and display the impact speed of a standard baseball dropped from 1 foot ± 0.25 inches. | (1) The on signal start time and off signal stop time are measured by an oscilloscope.<br>(2) The distance between layer 2 and layer 3 is measured by a scale of smallest resolution of 1/32 inch.<br>(3) The time difference between start and stop divided by the distance between layer 2 and 3 shall equal the TPM value.<br>(4) The TPM is observed on the display. |
| 1.3 | The system shall measure and display the impact speed of a standard baseball dropped from 5 feet ± 1.25 inches. | (1) The on signal start time and off signal stop time are measured by an oscilloscope.<br>(2) The time difference between start and stop divided by the distance between layer 2 and 3 shall equal the TPM value.<br>(4) The TPM is observed on the display. |

FIG. 8A

| ID | Requirement | Verification Description |
|---|---|---|
| 1. | Technical | |
| 1.4 | The system shall measure and display the impact speed of a standard baseball dropped from 10 feet ± 1.25 inches. | (1) The on signal start time and off signal stop time are measured by an oscilloscope.<br>(2) The time difference between start and stop divided by the distance between layer 2 and 3 shall equal the TPM value.<br>(4) The TPM is observed on the display. |
| 1.5 | The system shall measure the impact speed of a martial arts stick striking a round training bag. | |

FIG. 8B

PRODUCT IDENTIFICATION
Product Trade Name: Statfree® Conductive Foam
Chemical Family: Polyolefin
Chemical Name: Polyethylene Foam
Other Names: LD Conductive (CN) or Static Dissipative (SD) Grades
CAS Name & Number:   Polyethylene CAS 9002-88-4
                               Carbon Black CAS 1333-88-4

COMPOSITION
Crosslinked polyethylene: 90-93%
Carbon black: 7-10%

PHYSICAL DATA
Density: 0.92 g/cc (polymer)
Bulk Density (kg/m$^3$): Nominal densities vary from 30 Kg/m$^3$ to 50 Kg/m$^3$

FIG. 9

SPEED TRACKER

REFERENCE TO RELATED APPLICATIONS

This application claims the benefit of Provisional Application No. 62/395,887, filed Sep. 16, 2016, the contents of which are incorporated herein by reference.

FIELD OF THE INVENTION

The present invention relates generally to a device for measuring, transmitting and displaying on a computer or mobile display device, the speed, force, rate and/or frequency of impact of an object hitting a target. In one preferred embodiment, the present invention is used to measure, transmit and display on a computer or cell phone, the speed, force, rate and/or frequency of impact of a person striking a self-defense training target.

BACKGROUND OF THE INVENTION

"Strike targets" are used in self-defense training. The targets absorb blows from various body parts of a self-defense training participant. These targets may be hand held or floor or wall mounted, they may be stationary or moving, they may look like the torso of a human body, a punching bag or some other shape.

These targets have advantages and disadvantages. A hand held target requires a second person to hold the target. The person holding the target is able to provide at least some limited feedback to the participant based on the sensory perceptions of the target holder, but such observations are usually imprecise. A stationary target does not require a second person to hold it, but offers no feedback to the participant.

One prior art device created by Applicant is illustrated in FIGS. 1 and 2. The device utilizes a non-contact sensors, such as a laser, for measuring and transmitting the speed of an object hitting a target. This measurement is wirelessly transmitted to a computer or cell phone for display. The prior art device has some shortcomings, as the laser must be pointed precisely where a trainer strikes a training bag. People have different shapes and heights and do not strike the bag in the same place or even consistently strike the bag in the same place. This results in poor measurements or no measurements at times. Further, the laser is focused on a particular location and the speed measured is only the speed of a body part at that instant, not necessarily the strike force on the bag.

Thus, there remains a need for a target that does not require an extra person to hold the device and which will give consistently accurate information to the self-defense training participant about the strike force, speed and rate.

SUMMARY OF THE INVENTION

The present invention is a device for measuring and displaying the speed, force and/or rate an object or a body part strikes a target. The present invention includes a sensor, computer, transmitter and a display.

The sensor of the present invention consists of a first and second layer of conductive fabric separated by a layer of perforated, non-conductive fabric. The distance between the conductive layers is known. Upon striking the first conductive fabric layer, the conductive fabric generates an electric signal that is transmitted to a computer, such as a laptop/desktop, cell phone, tablet or similar device, indicating the time of the initial strike.

The force of the strike causes portions of the first conductive layer of fabric come into contact with portions of the second conductive fabric layer through the perforations in the non-conductive material. When this occurs, the first and/or second conductive layers generate an electric signal that is transmitted to the computer indicating the time of contact. An algorithm is applied to these signals/data in light of the distance between the two conductive fabric layers to determine the speed, force and/or rate of the strike. This information is then displayed on the display device.

The display system of the present invention is typically the computer but can be some other device. The computer can be in direct electric communication with the conductive fabric or in wireless communication. The wireless system includes a communication device in electric communication with the conductive fabrics for receiving signals from the fabric. The communication device either interprets the signals from the conductive fabrics and wirelessly transmits the interpreted data to the computer for display or simply transmits the data obtained from the conductive fabrics to the computer for interpretation and display.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 7 is a table of specifications of preferred electrically conducive fabrics;

FIG. 8A is a table illustrating the design performance and characteristics of one preferred embodiment of the present invention;

FIG. 8B is a continuation of the table of FIG. 8A; and

FIG. 9 is a table showing characteristics of one preferred embodiment of a fabric utilized in the present invention.

DETAILED DESCRIPTION OF THE INVENTION

Figure 1:
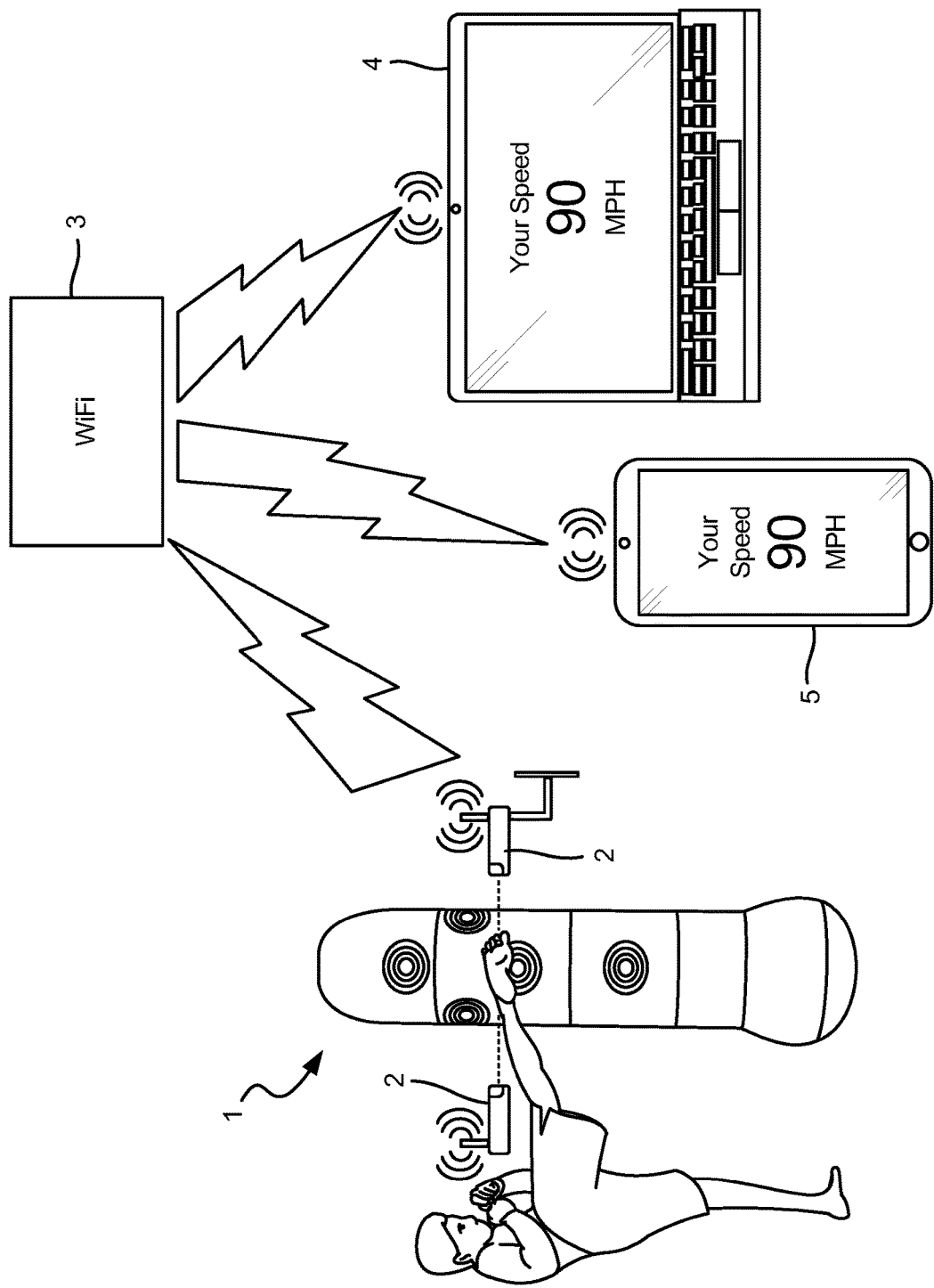
FIG. 1 is a flow diagram illustrating the general components and operation of the prior art.

Applicant developed a prior art device for measuring the speed of a kick against a training bag, as shown in FIGS. 1 and 2. This device includes the use of a strike target 1, two opposing laser transmitters/receivers 2, WIFI or other wireless connection 3 and a display device (computer 4 or phone 5).

Figure 2:
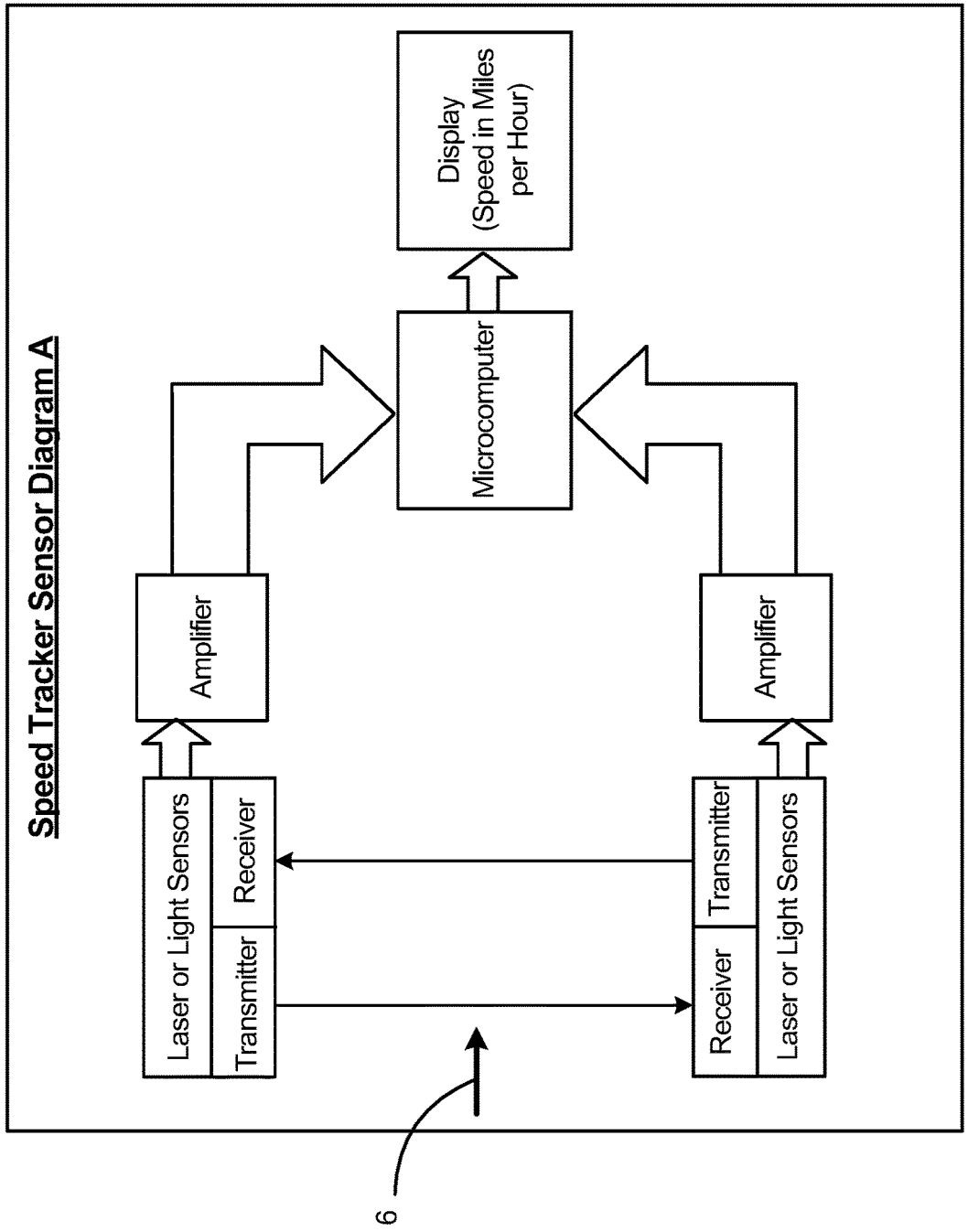
FIG. 2 is a flow diagram illustrating the general operation of the prior art.

Each laser device includes a transmitter/receiver in spaced relation that corresponds with a receiver/transmitter on the other laser as shown in FIG. 2. Each transmitter sends a signal to the receiver on the opposing laser, creating two spaced constant signals.

In operation, a trainee kicks target 1 between the lasers 2. As shown in FIG. 2, the kick in the direction of arrow 6 breaks the first signal, causing one of the lasers to send a first message to the microcomputer. As the kick progresses in the direction of arrow 6, the second signal is broken, causing one of the lasers to send a second message to the microcomputer. At the microcomputer, an algorithm is applied, based on the distance between the first and second laser signals and the time differential measured between the breaking of the first and second signals, to calculate the speed of the strike.

The prior art device has a number of disadvantages. The lasers are quite expensive and heavy and require constant adjustment and calibration since people of different sizes and shapes strike the target at different heights. (Each participant may strike the target at a different height throughout training as well.) This results in poor measurements or non-measurements of the strike. Additionally, the lasers, if struck by a trainee, can be damaged or cause harm to the trainee.

In contrast, the present invention 10 requires less equipment, dramatically reduces the weight and cost of the system, requires no calibration or adjustment, does not present any obstacles that could harm a trainee and improves the ease of moving the system.

Figure 3:
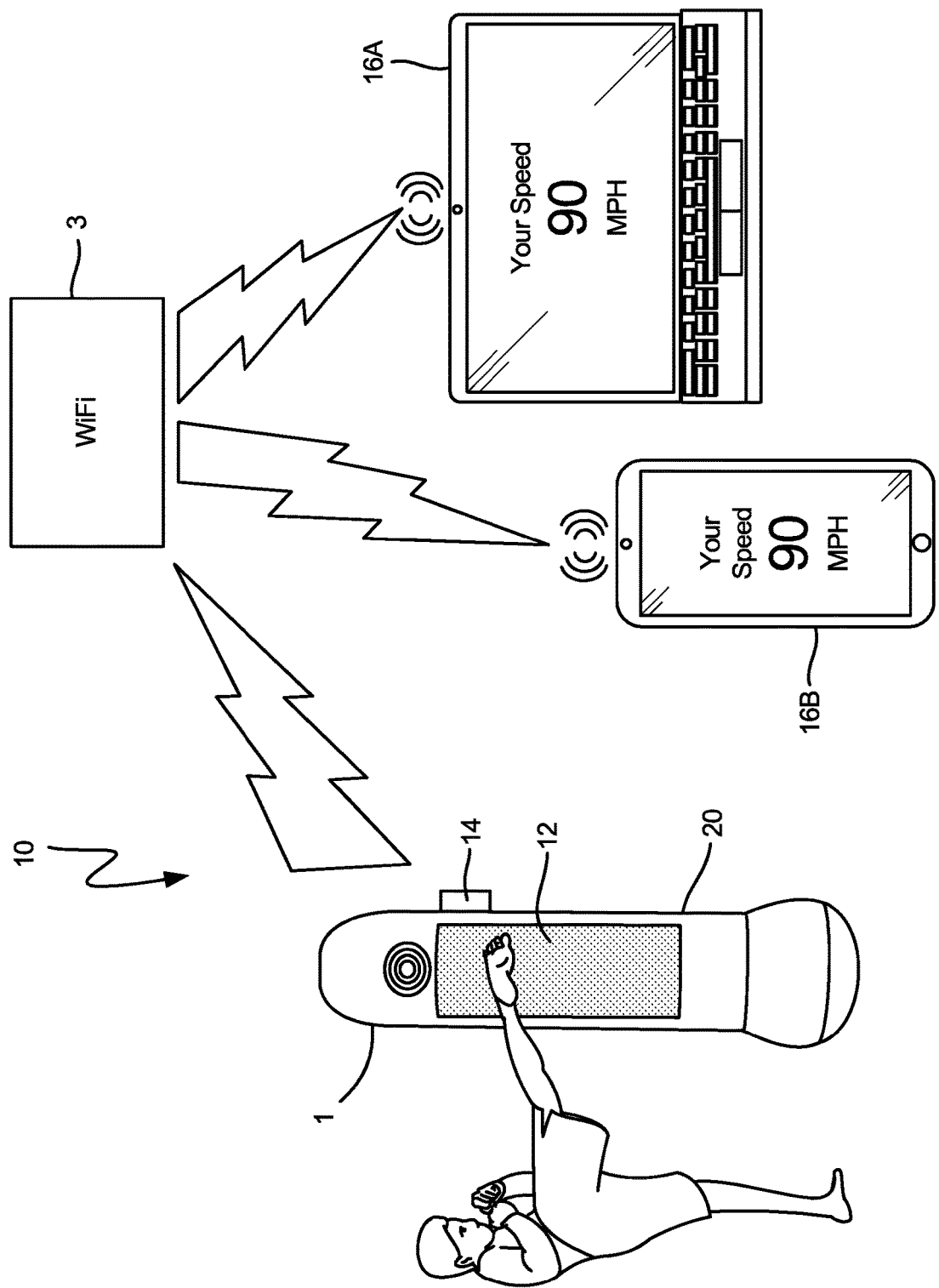
FIG. 3 is a flow diagram illustrating the general components and operation of one embodiment of the present invention.

The present invention operates in a similar fashion as the prior art but instead of the heavy, high maintenance and expensive lasers, the present invention utilizes a sensor attached to the target to measure speed, force and rate of a strike. In one preferred embodiment shown in FIG. 3, the present invention includes a sensor 12 attached to target 20. The sensor is in electrical communication with a computer/wireless transmitter 14 which communicates wirelessly with display 16 (desktop or laptop computer 16A or cell phone or other portable display device 16B) having a wireless receiver.

Figure 4:
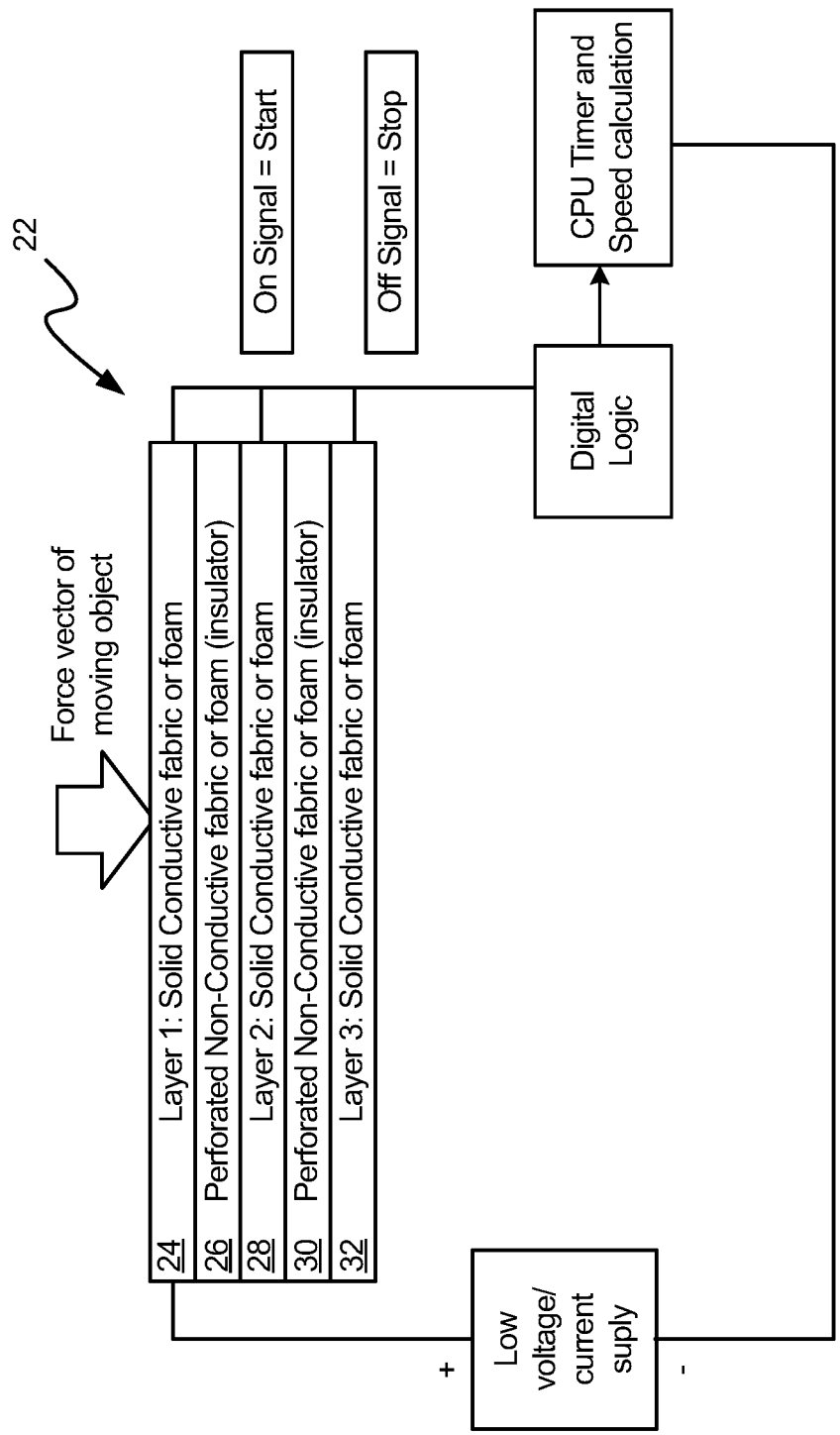
FIG. 4 illustrates the alternating layers of conductive and non-conductive material utilized in the present invention.

Sensor 12 consists of layers of alternating conductive 24, 28, 32 and non-conductive 26, 30 material or fabric as diagramed in FIG. 4. The layered fabric is attached to, wrapped around or forms the skin of the target. (As illustrated, the fabric covers a significant portion of the bag 1 so that people of all sizes are likely to strike the fabric portion of the bag on each hit or strike.)

The conductive layers are responsive to a strike, such that an electrical signal is generated and transmitted to the computer/transmitter.

Figure 5:
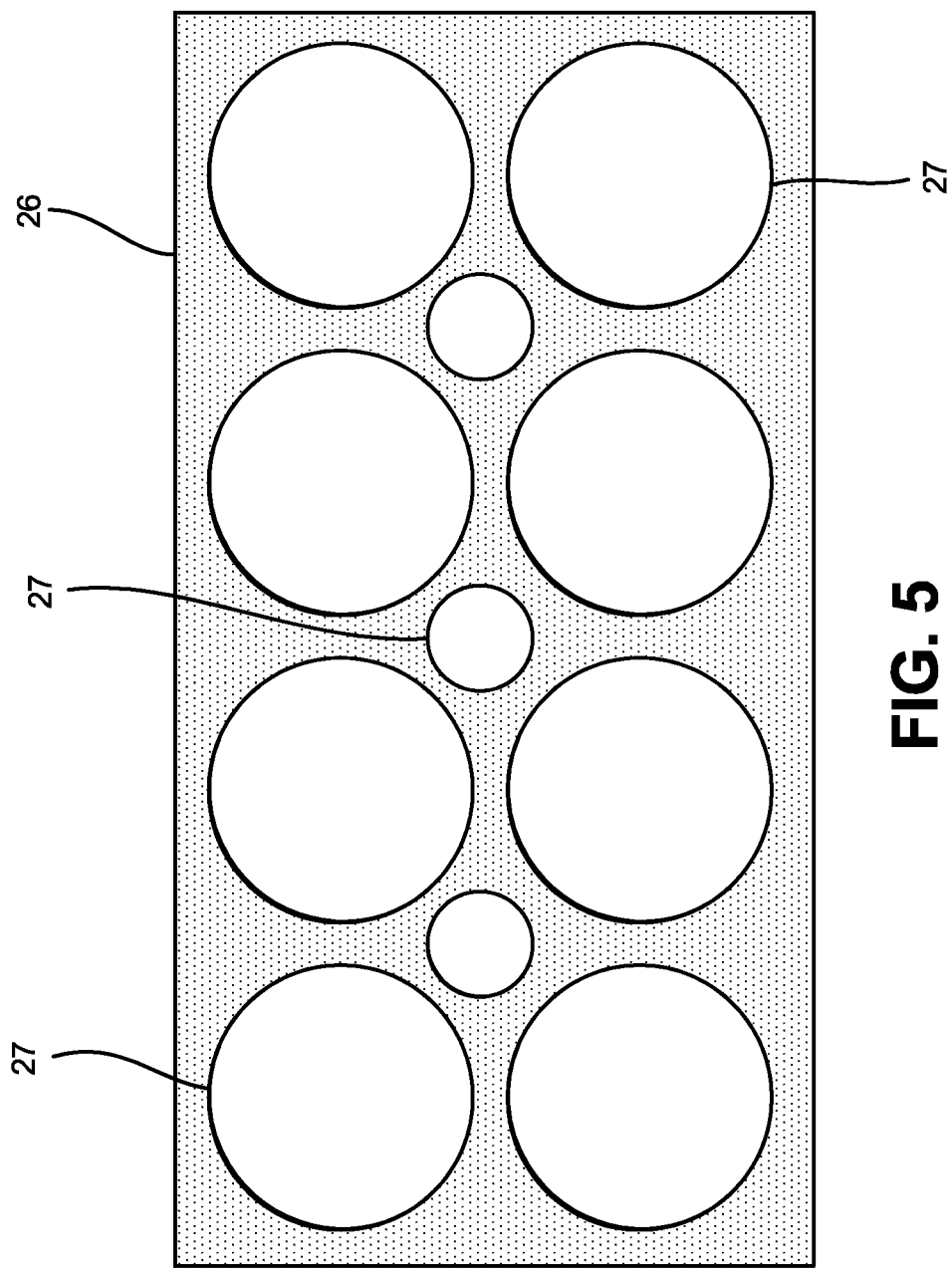
FIG. 5 illustrates a side view of the non-conductive fabric of the present invention.
Figure 6:
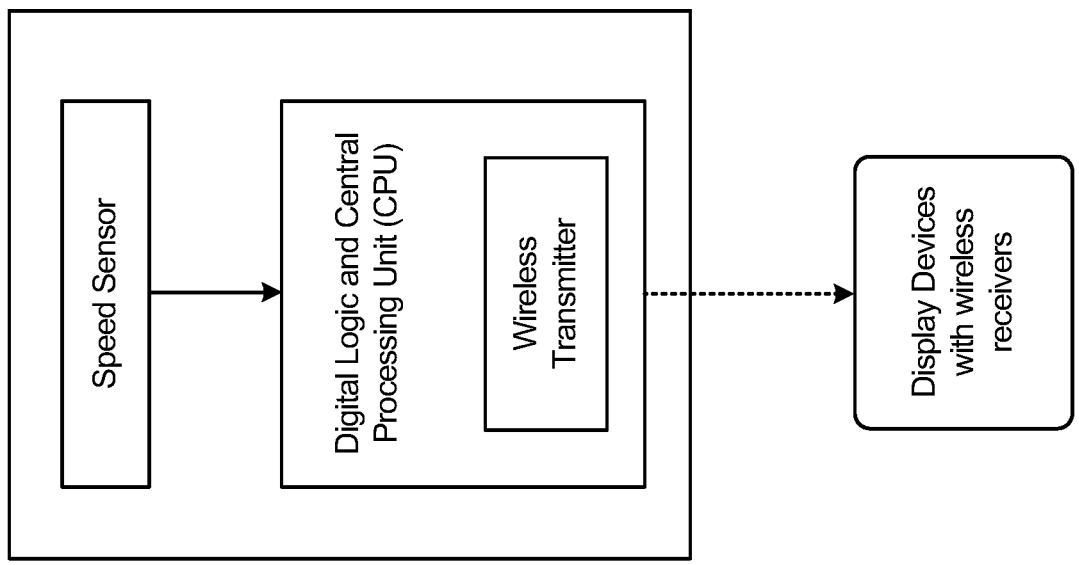
FIG. 6 is a flow diagram illustrating how signals generated by striking an object are transmitted from a sensor to a CPU where the signals are algorithmically interpreted and the resulting data is wirelessly transmitted for display on a display device.

In one preferred embodiment, the layered fabric of sensor 12 includes at least two layers of conductive fabric, cloth or foam 24 and 28 (first and third layers) separated by a perforated, non-conductive fabric, cloth or foam layer 26 (shown in side view in FIG. 5). In another preferred embodiment, the fabric may include additional layers of conductive material separated by non-conductive material, as shown at 30 and 32 in FIG. 4. The conductive layers of fabric generate electrical impulses when struck and serve as data points that are interpreted by the computer to derive information about the strike against the target.

The distance between the conductive layers is defined by the width of the non-conductive fabric. Upon striking the first conductive fabric layer 24, the conductive fabric sends an electrical signal to the computer/transmitter 14 setting an initial strike time. The force of the strike causes portions of the first conductive layer of fabric 24 to come into contact with portions of the second conductive fabric layer 28 through perforations or openings 27 in the non-conductive material 26. When this occurs, electrical impulses from the first or second conductive layers 24, 28 are sent to the computer/transmitter 14 to identify the time of the second strike. An algorithm is applied to this data based on the distance between the two conductive fabric layers and the time differential between the first and second signals to determine the speed, force, rate and/or frequency of the strike (and such additional information as can be derived using the fabric and computer of the present invention). (Alternatively, the first and second signals act as an "on" and "off" switch to record the time differential between the first and second signals.) This information is then transmitted to and displayed on the display device in usable form. Such impact information/statistics can be displayed in any desired units, i.e. miles per hours or kilometers per hour for speed.

The width of the non-conductive layer of fabric 26 can be pre-established to assist in the measurement of the time between contact with the first fabric layer and the second fabric layer. Alternatively, as shown in FIG. 5, multiple layers of alternating conductive and non-conducting fabric can be utilized with multiple data points (signals from the conductive fabric layers in response to the strike) to confirm or enhance the accuracy and completeness of the information obtained from the device.

One preferred fabric is Statfree® Conductive Foam identified by characteristics identified in FIG. 7 and FIG. 9. However, the present invention is not limited to such characteristics or fabric.

Some preferred functionality of the present invention is illustrated in FIGS. 8A and 8B, but again, such functionality is not limiting, only exemplary.

Strike target 20 shown in the drawings is a training bag, but there is no limitation on the strike targets to which the fabric (sensor) can be attached. The impact sensor may be mounted to impact devices or structures such as a punching bag, football blocking sled to measure player speed of impact with the sled, baseball backstops to measure the speed of a pitch, a tennis practice wall to measure the speed of a serve or return, among other possibilities.

In one preferred embodiment, the sensor computer/transmitter is mounted away from the strike zone of the fabric to protect it from damage and the trainee from harm.

In one preferred embodiment, more than one display can be synchronized with the sensor to display the impact data in a desired form.

In one preferred embodiment, the measuring device automatically resets in preparation for the next strike after the fabric signals are sent.

In one preferred embodiment, impact or strike data can be organized and saved in the computer/transmitter or display device for future reference and the data for each trainee can be organized to provide desired reports to trainees, instructors, observers and record keepers.

In one preferred embodiment, the sensor merely sends raw signals to the display and the display computer, which interprets the data and displays the strike information.

In one preferred embodiment, the fabric signals are transmitted to the display and the display interprets the data and displays the impact information.

Application of the technology of the present invention is not limited to sports. It is anticipated that the present invention is useful in any situation where it is desirable to know the speed, force, rate, frequency or other information regarding the impact of an object or body part against a target.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

The invention claimed is:

1. A device for measuring the speed of impact of an object striking a target, including:
   a. a sensor for mounting on a target, the sensor including a computer in electric communication with a layered fabric, the layered fabric including first second and third conductive fabrics, the first and second conductive fabrics being separated by a first layer of non-conductive fabric having one or more openings in the fabric, the second and third conductive fabrics being separated by a second non-conductive fabric having one or more openings in the fabric, the distance between the conductive fabrics being known,
   b. a display device in communication with the computer for displaying impact data;
   c. whereupon when an object strikes the first conductive fabric, the first conductive fabric is forced, through the openings in the first non-conductive fabric, into contact with the second conductive fabric, and a first set of data is transmitted through the first and second conductive fabrics to the computer, and the second conductive fabric is forced, through the openings in the second non-conductive fabric, into contact with the third conductive fabric, and a second set of data is transmitted through the second and third conductive fabrics to the computer, and an algorithm is applied to the first and second sets of data in light of the distance between the first and second conductive fabrics and the second and third conductive fabrics to determine the rate of impact of the object with the fabrics, which is then displayed on the display device.

2. The device for measuring the speed of impact of an object striking a target of claim 1 wherein the algorithm derives one or more of the speed, force, rate and frequency of the impact.

3. The device for measuring the speed of impact of an object striking a target of claim 1 wherein the impact measuring device automatically resets in preparation for the next strike after the fabric signals are sent.

4. The device for measuring the speed of impact of an object striking a target of claim 1 wherein the non-conductive fabric is interchangeable to permit application of different widths of non-conductive fabric.

5. The device for measuring the speed of impact of an object striking a target of claim 1 wherein the display device is a cell phone.

6. The device for measuring the speed of impact of an object striking a target of claim 1 wherein the display device is a personal computer.

7. The device for measuring the speed of impact of an object striking a claim 1 wherein the sensor computer is mounted away from the strike zone of the fabric.

8. The device for measuring the speed of impact of an object striking a target of claim 1 wherein more than one display can be synchronized with the sensor to display the impact data in a desired form.

9. The device for measuring the speed of impact of an object striking a target of claim 1 wherein impact data can be organized and saved in the computer or display device for future reference.

10. The device for measuring the speed of impact of an object striking a target of claim 1 wherein data for each trainee can be organized to provide desired reports.

11. The device for measuring the speed of impact of an object striking a target of claim 1 wherein the fabric signals are transmitted to the display and the display interprets the data and displays the impact information.

12. A target that measures the speed of impact of an object, including:
   a. a sensor including a computer in electric communication with a layered fabric, the layered fabric including first second and third conductive fabrics, the first and second conductive fabrics being separated from each other by a first non-conductive fabric having one or more openings, and the second and third conductive fabrics being separated from each other by a second non-conductive fabric having one or more openings, the distance between the conductive fabrics being known,
   b. a display device in communication with the computer for displaying impact data; whereupon when an object strikes the first conductive fabric, it is forced through the opening in the first non-conductive fabric into contact with the second conductive fabric, to transmit a first set of data to the computer, and the second conductive fabric is forced through the opening in the second non-conductive fabric into contact with the third conductive fabric, to transmit a second set of data to the computer, and an algorithm is applied to the first and second sets of data in light of the distance between the first and second fabric layers to determine the rate of impact of the object, which is then displayed on the display device.

* * * * *